(12) United States Patent
Krizmanić et al.

(10) Patent No.: US 8,153,790 B2
(45) Date of Patent: Apr. 10, 2012

(54) PROCESS FOR THE PREPARATION AND PURIFICATION OF ETRAVIRINE AND INTERMEDIATES THEREOF

(76) Inventors: Irena Krizmanić, Sisak (HR); Jasna Dogan, Zagreb (HR); Marina Marinković, Sesvete-Zagreb (HR); Maja Šepelj, Rijeka (HR)

(*) Notice: Subject to any disclaimer, the term of this patent is extended or adjusted under 35 U.S.C. 154(b) by 0 days.

(21) Appl. No.: 13/131,698

(22) PCT Filed: Jul. 27, 2010

(86) PCT No.: PCT/US2010/043329
§ 371 (c)(1),
(2), (4) Date: Jul. 19, 2011

(87) PCT Pub. No.: WO2011/017079
PCT Pub. Date: Feb. 10, 2011

(65) Prior Publication Data
US 2011/0275812 A1    Nov. 10, 2011

Related U.S. Application Data

(60) Provisional application No. 61/228,804, filed on Jul. 27, 2009, provisional application No. 61/249,423, filed on Oct. 7, 2009, provisional application No. 61/264,045, filed on Nov. 24, 2009, provisional application No. 61/287,427, filed on Dec. 17, 2009.

(51) Int. Cl.
*C07D 239/02* (2006.01)
(52) U.S. Cl. .................. 544/317; 544/319; 544/321
(58) Field of Classification Search ............... 544/317, 544/321, 316, 319
See application file for complete search history.

(56) References Cited

U.S. PATENT DOCUMENTS

| | | | |
|---|---|---|---|
| 7,037,917 B2 | 5/2006 | De Corte et al. | |
| 7,276,510 B2 * | 10/2007 | Kukla et al. | 514/272 |
| 2008/0176880 A1 | 7/2008 | De Corte et al. | |
| 2009/0105147 A1 | 4/2009 | Masse | |

FOREIGN PATENT DOCUMENTS

| | | |
|---|---|---|
| WO | WO-99/50250 A1 | 10/1999 |
| WO | WO-00/27825 A1 | 5/2000 |
| WO | WO-01/85699 A2 | 11/2001 |
| WO | WO-01/85700 A2 | 11/2001 |
| WO | WO-2006/045828 A1 | 5/2006 |
| WO | WO-2006/079656 A1 | 8/2006 |
| WO | WO-2006/087387 A1 | 8/2006 |
| WO | WO-2006/094930 A1 | 9/2006 |
| WO | WO-2008/071587 A2 | 6/2008 |
| WO | WO-2008/080964 A1 | 7/2008 |
| WO | WO-2010/150279 A2 | 12/2010 |

OTHER PUBLICATIONS

Delia et al. (J. Heterocyclic Chem., 35, 269 (1998).*
Davies, S. L., et al., "Etravirine, Anti-HIV Agent Reverse Phase Inhibitor", *Drugs of the Future*, 2005, vol. 30, No. 5, pp. 462-468.
De Spiegeleer, Bart, et al., "Synthesis and HPLC-purification of [77Br]TMC125-R165335 (etravirine), a new anti-HIV drug of the DAPY-NNRTI class", *J. Label. Compd. Radiopharm.*, 2006, vol. 49, pp. 683-686.
Ludovici, D. W., et al., "Evolution of anti-HIV drug candidates. Part 3: diarylpyrimidine (DAPY) analogues", *Bioorg. Med. Chem. Lett.*, 2001, vol. 11, pp. 2235-2239.
Joshi, Shashikant, et al., "An improved synthesis of etravirine", Organic Process Research & Development, Apr. 21, 2010, vol. 14, No. 2, pp. 657-660.

* cited by examiner

*Primary Examiner* — Andrew D Kosar
*Assistant Examiner* — Valerie Rodriguez-Garcia
(74) *Attorney, Agent, or Firm* — Kenyon & Kenyon LLP

(57) ABSTRACT

In one embodiment the present invention encompasses 4-(2,6-dichloropyrimidin-4-yloxy)-3,5-dimethylbenzonitrile ("ETHER"), 4-(4,6-dichloropyrimidin-2-yloxy)-3,5-dimethyl-benzonitrile ("ETHER C-2 isomer"), mixtures and salts thereof of. The present invention encompasses the use of ETHER and salts thereof to prepare Etravirine and Etravirine intermediates, and salts thereof. In another embodiment the present invention encompasses the use of ETHER and salts thereof to prepare debrometravirine ("DEBETV") and salts thereof. In yet another embodiment the present invention encompasses the use of ETHER and salts thereof to prepare 4-(6-chloro-2-(4-cyanophenylamino)pyrimidin-4-yloxy)-3,5-dimethyl-benzonitrile ("ARCPBN") and salts thereof. The compound, 4-(2,6-dichloropyrimidin-4-yloxy)-3,5-dimethylbenzonitrile "ETHER" of formula (A) wherein n is either 0 or 1 and HA is an acid.

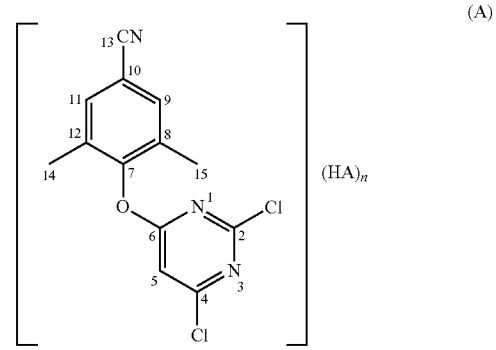

(A)

26 Claims, 11 Drawing Sheets

PROCESS FOR THE PREPARATION AND PURIFICATION OF ETRAVIRINE AND INTERMEDIATES THEREOF

CROSS REFERENCE TO RELATED APPLICATIONS

The present application claims the benefits of the following U.S. Provisional Patent Application Nos. 61/228,804 filed Jul. 27, 2009; 61/249,423 filed Oct. 7, 2009; 61/264,045 filed Nov. 24, 2009; and 61/287,427 filed Dec. 17, 2009. The contents of these applications are incorporated herein by reference.

FIELD OF THE INVENTION

The present invention relates to a process of preparation and purification of Etravirine and intermediates thereof.

BACKGROUND OF THE INVENTION

Etravirine ("ETV"), 4-(6-amino-5-bromo-2-(4-cyanophenylamino)pyrimidin-4-yloxy)-3,5-dimethylbenzonitrile of the following chemical structure:

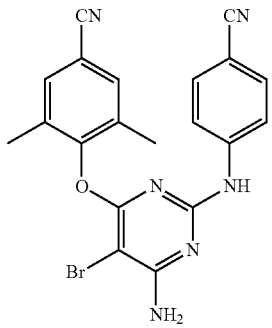

is a drug used for the treatment of HIV.

Etravirine is formerly known as TMC-125, brand name Intelence®.

Etravirine, its analogs and their synthesis are described in U.S. Pat. No. 7,037,917. In this patent Etravirine is prepared by reacting a tetrahoganated pyrimidine derivative and aminobenzene derivative, and optionally brominating the obtained compound, to obtain Etravirine. This process includes two steps of chromatographic purification of Etravirine's intermediates, and the final product is obtained in very poor overall yield.

EP 945443 claims a general process for the preparation of anilinopyrimidine derivatives, and salts thereof, e.g., by aminolysis reactions of pyrimidine compounds containing leaving groups.

Bioorg. Med. Chem. Lett. 11 (2001) 2235-2239 describes a process for preparing Etravirine, according to the following scheme:

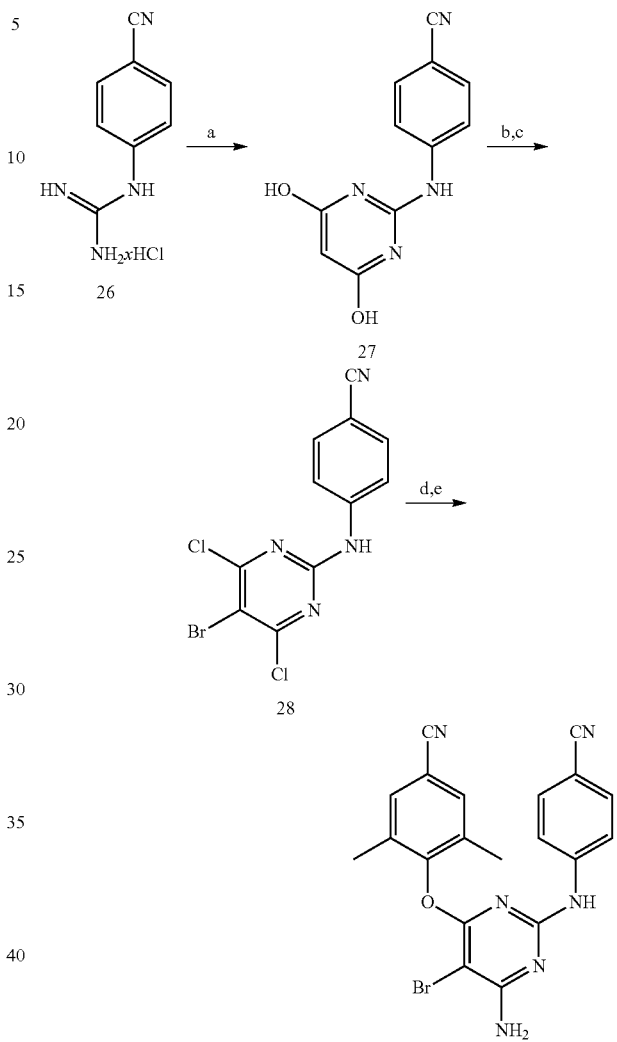

(a) Diethyl malonate, NaOEt in EtOH, 76%;
(b) POCL$_3$, 86%;
(c) Br$_2$ NaHCO$_3$, H$_2$O, MeOH, 78%;
(d) sodium 4-cyano$^{2,6}$-dimethylphenolate, NMP, 1,4-dioxane, 45%;
(e) NH$_3$i-PrOH, 41%.

where Etravirine is obtained in a very poor overall yield of less than 10%.

WO 01/85700 describes preparation of Etravirine analogues, which do not include an NH$_2$ group. In this process, Etravirine analogues are also purified by column chromatography and are obtained in very poor overall yield of about 2-5%.

WO 2006/094930, WO 2008/071587 and WO 2000/027825 describe different processes for preparation of different Etravirine intermediates and derivatives, all of which require at least one chromatographic purification step.

WO 2008/068299 discloses that Etravirine has very poor solubility in water, and describes a hydrobromide salt of Etravirine, which is prepared by dissolving Etravirine in dichloromethane and reacting with hydrobromic acid.

The present invention addresses the need to obtain debrometravirine ("DEBETV") and Etravirine in high yield and purity, in a method that can be adapted to industrial scale. The present invention provides a new synthesis of Etravirine, via a novel intermediate, 4-(2,6-dichloropyrimidin-4-yloxy)-3, 5-dimethylbenzonitrile ("ETHER"). Also described are purification processes for DEBETV and Etravirine.

SUMMARY OF THE INVENTION

In one embodiment the present invention encompasses 4-(2,6-dichloropyrimidin-4-yloxy)-3,5-dimethylbenzonitrile ("ETHER"), 4-(4,6-dichloropyrimidin-2-yloxy)-3,5-dimethylbenzonitrile ("ETHER C-2 isomer"), mixtures and salts thereof of the following structure:

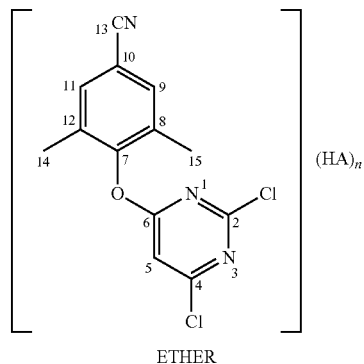

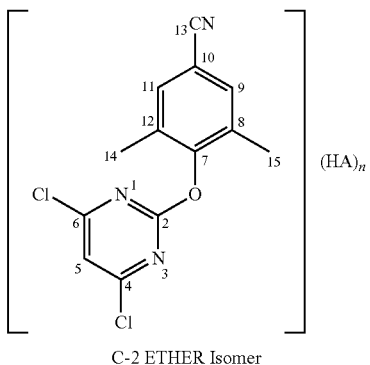

wherein n is either 0 or 1 and HA is an acid.

In another embodiment the present invention encompasses the use of ETHER and salts thereof to prepare Etravirine and Etravirine intermediates, and salts thereof.

In another embodiment the present invention encompasses the use of ETHER and salts thereof to prepare debrometavirine ("DEBETV") and salts thereof.

In yet another embodiment the present invention encompasses the use of ETHER and salts thereof to prepare 4-(6-chloro-2-(4-cyanophenylamino)pyrimidin-4-yloxy)-3,5-dimethylbenzonitrile ("ARCPBN") and salts thereof.

In another embodiment the present invention encompasses a process for preparing ETHER and salts thereof comprising reacting 2,4,6-trihalopyrimidine ("ThalP") of the following structure:

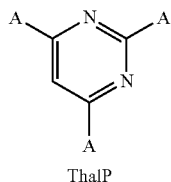

and 4-hydroxy-3,5-dimethylbenzonitrile (DMHB) of the following structure:

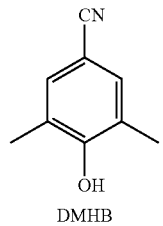

wherein each of A is preferably a halogen atom, and more preferably chlorine.

In yet another embodiment the present invention encompasses a process for preparing Etravirine comprising preparing ETHER and salts thereof by the process of the present invention and converting it to Etravirine and salts thereof.

In another embodiment the present invention encompasses a process for preparing 4-(6-chloro-2-(4-cyanophenylamino)pyrimidin-4-yloxy)-3,5-dimethylbenzonitrile ("ARCPBN") comprising reacting ETHER and salts thereof and 4-aminobenzonitrile (ABN) of the following formula:

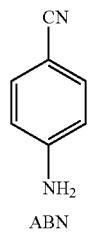

In yet another embodiment the present invention encompasses a process for preparing Etravirine comprising preparing ARCPBN by the process of the present invention and converting it to Etravirine and salts thereof.

In one embodiment the present invention encompasses a process for the purification of the compound of formula I of the following structure:

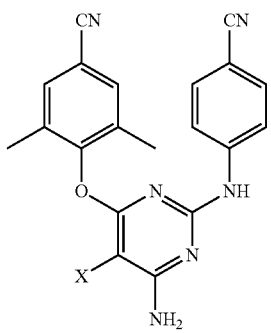

comprising reacting a salt of the compound of formula I and a base in a mixture of water and a water miscible organic solvent; wherein X is either H or Br; when X is H the water miscible organic solvent is 1-propanol and when X is Br the water miscible organic solvent is acetone.

In yet another embodiment the present invention encompasses a process for the preparation of Etravirine comprising purifying the salt of the compound of formula Ia of the following structure:

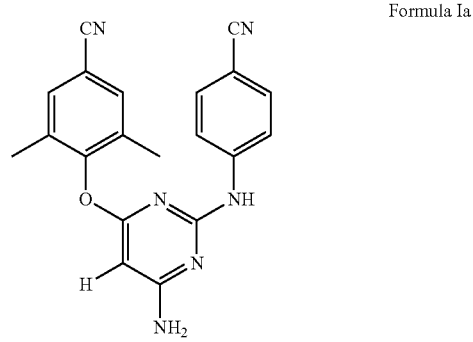

Formula Ia according to the process of the present invention, and converting it to Etravirine and salts thereof.

DETAILED DESCRIPTION OF THE INVENTION

The present invention addresses the need to obtain debrometravirine ("DEBETV") and Etravirine in high yield and purity, in a method that can be adapted to industrial scale. The present invention offers a new synthesis of Etravirine, via an intermediate named 4-(2,6-dichloropyrimidin-4-yloxy)-3,5-dimethylbenzonitrile ("ETHER") and salts thereof.

The present invention also describes purification processes for DEBETV and Etravirine.

The methods for preparing Etravirine and Etravirine derivatives provided in the literature provide the final product in very poor yield, and often require chromatographic purification.

As used herein, the term "room temperature" refers to a temperature between about 20° C. and about 30° C. Usually, room temperature ranges from about 20° C. to about 25° C.

As used herein, the term "overnight" refers to a period of between about 15 and about 20 hours, typically between about 16 to about 20 hours.

A crystal form may be referred to herein as being characterized by graphical data "substantially as depicted in" or "as depicted in" a Figure. Such data include, for example, powder X-ray diffractograms and solid state NMR spectra. The skilled person will understand that such graphical representations of data may be subject to small variations, e.g., in peak relative intensities and peak positions due to factors such as variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms.

As used herein, the term water miscible solvent relates to a solvent which forms a one phase mixture when combined with water.

The present invention provides a process for preparing Etravirine and salt thereof from an intermediate named 4-(2,6-dichloropyrimidin-4-yloxy)-3,5-dimethylbenzonitrile ("ETHER").

In one embodiment the present invention encompasses 4-(2,6-dichloropyrimidin-4-yloxy)-3,5-dimethylbenzonitrile ("ETHER"), 4-(4,6-dichloropyrimidin-2-yloxy)-3,5-dimethylbenzonitrile ("ETHER C-2 isomer") and salts thereof of the following structure:

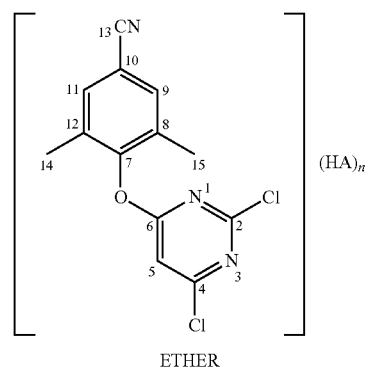

ETHER

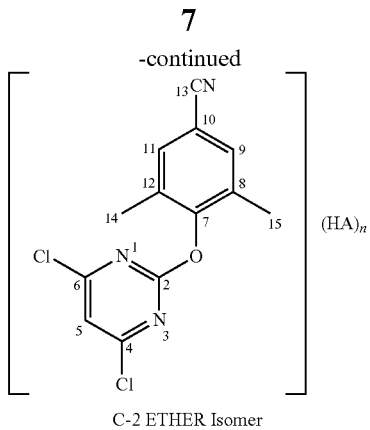

C-2 ETHER Isomer wherein n is either 0 or 1 and HA is an acid. The acid can be, for example, HCl, HBr, HF, HI, p-toluenesulfonic acid ("PTSA"), nitric acid, phosphoric acid, benzesulfonic acid or ethanesulfonic acid.

In a preferred embodiment, the above ETHER and C-2 ETHER isomer is a mixture, which is provided in an isolated form. Preferably, the isolated ETHER or C-2 ETHER isomer is solid.

As used herein, the term "isolated" in reference to the mixture of ETHER and C-2 ETHER isomer corresponds to ETHER or C-2 ETHER isomer that is physically separated from the reaction mixture, where it is formed.

Figure 1:
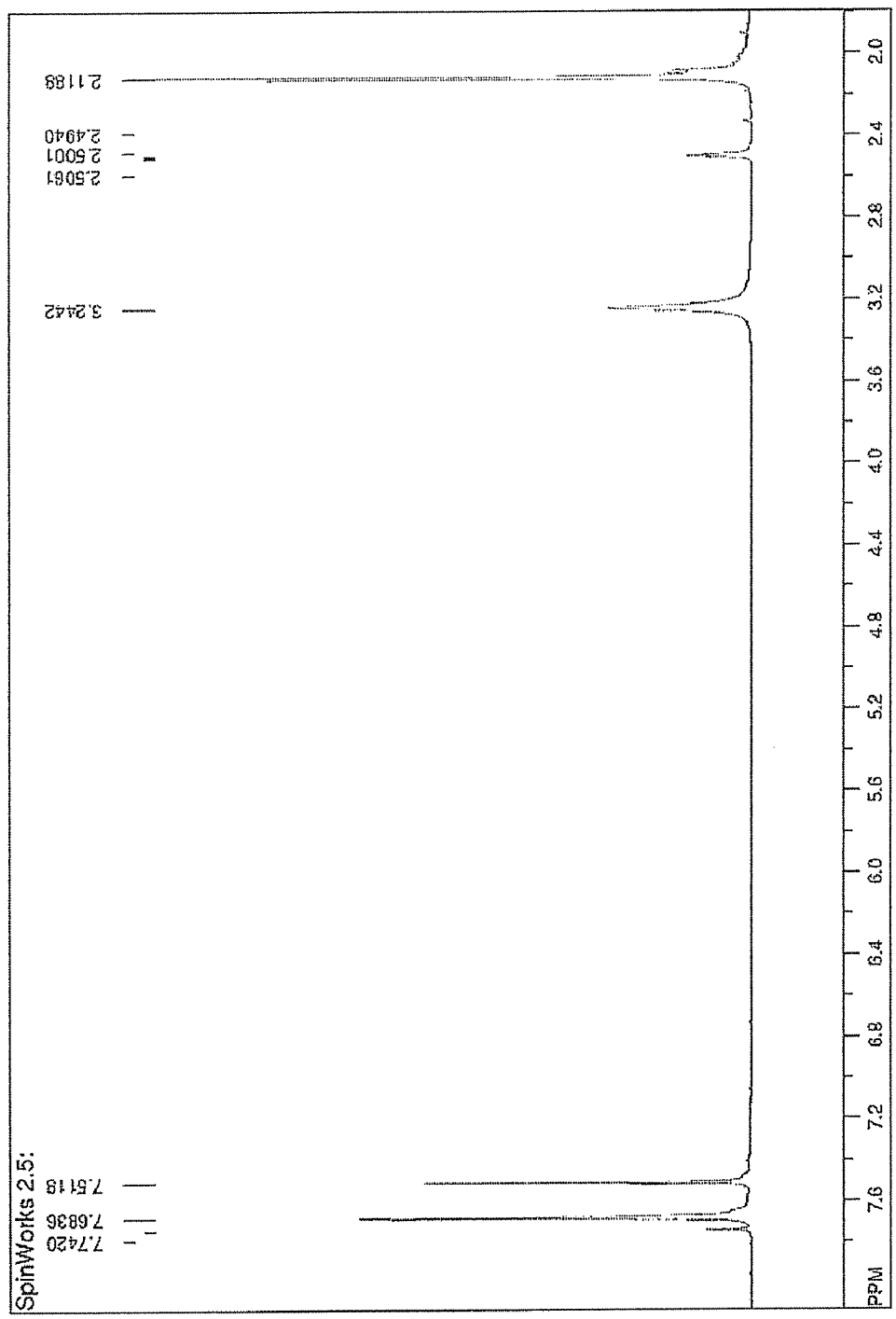
FIG. 1 illustrates $^1$H NMR pattern of a mixture of 4-(2,6-dichloropyrimidin-4-yloxy)-3,5-dimethylbenzonitrile ("ETHER") and 4-(4,6-dichloropyrimidin-2-yloxy)-3,5-dimethylbenzonitrile ("ETHER C-2 isomer").
Figure 2:
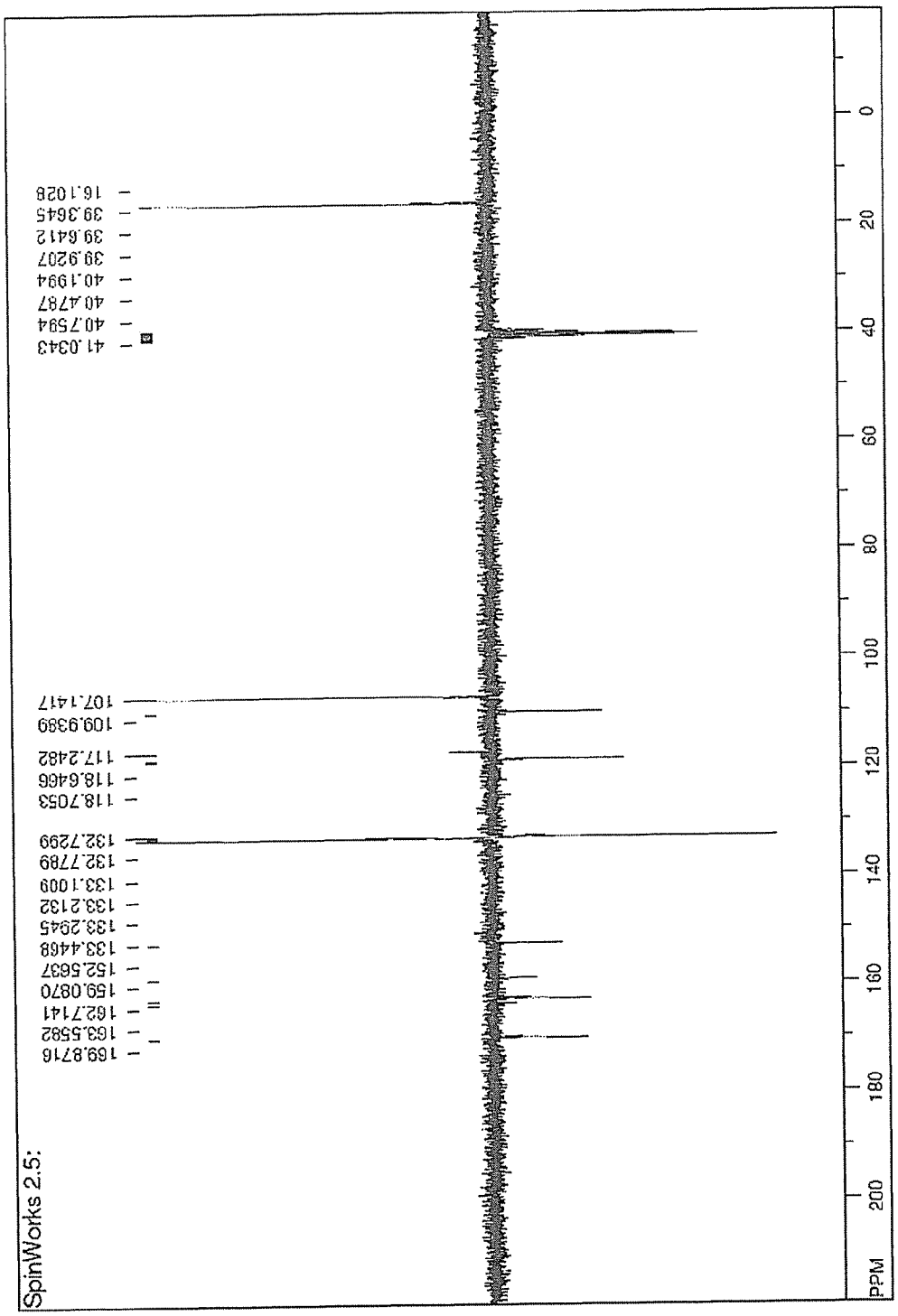
FIG. 2 illustrates $^{13}$C NMR pattern of a mixture of 4-(2,6-dichloropyrimidin-4-yloxy)-3,5-dimethylbenzonitrile ("ETHER") and 4-(4,6-dichloropyrimidin-2-yloxy)-3,5-dimethylbenzonitrile ("ETHER C-2 isomer").

The compound, ETHER, can be characterized by data selected from: $^1$H NMR (600.1 MHz, DMSO-d$_6$,), δ/ppm, having peaks at about 7.69 (2H, br), 7.52 (1H, s), and 2.12 (6H, s); $^1$H NMR pattern as depicted in FIG. 1; a $^{13}$C NMR (150.9 MHz, DMSO-d$_6$,), δ/ppm, having peaks at about 169.9 (C, s), 162.7 (C, s), 159.1 (C, s), 152.6 (C, s), 133.3 (CH, d), 132.8 (C, s), 118.7 (C, s), 109.9 (C, s), 107.1 (CH, d), and 16.1 (CH$_3$, q); a $^{13}$C NMR pattern as depicted in FIG. 2; and combinations thereof.

The compound, C-2 ETHER, isomer can be characterized by data selected from: $^1$H NMR (600.1 MHz, DMSO-d$_6$,), δ/ppm, having peaks at about 7.75 (1H, s), 7.69 (2H, br), and 2.12 (6H, s); $^1$H NMR pattern as depicted in FIG. 1; a $^{13}$C NMR (150.9 MHz, DMSO-d$_6$,), δ/ppm, having peaks at about 169.9 (C, s), 163.6 (2C, s), 152.6 (C, s), 133.2 (C, d), 132.7 (C, s), 118.7 (C, s), 117.3 (CH, d), 109.9 (C, s), and 16.1 (CH$_3$, q); a $^{13}$C NMR pattern as depicted in FIG. 2; and combination thereof.

The above ETHER, C-2 ETHER isomer, their mixture and salts thereof can be prepared by a process comprising reacting 2,4,6-trihalopyrimidine ("ThalP") of the following structure:

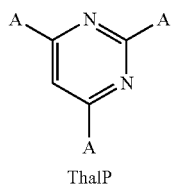

ThalP and 4-hydroxy-3,5-dimethylbenzonitrile (DMHB) of the following structure:

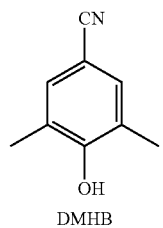

DMHB wherein each of A is independently a halogen, such as Cl.

In another embodiment, the above process comprises reacting 2,4,6-trisubstituted-pyrimidine (TsubP) and 4-hydroxy-3,5-dimethylbenzonitrile (DMHB), wherein the three substituents at the 2, 4 and 6 positions of the pyrimidine group are A, wherein each A is independently a halogen, preferably chlorine. Alternatively, 2,4,6-trisubstituted-pyrimidine (TsubP) of the following formula:

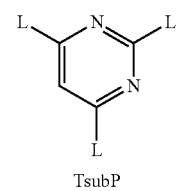

TsubP wherein each of L is independently a suitable leaving group and DMHB are reacted. As used herein, unless otherwise noted, the term "leaving group" shall refer to any charged or uncharged atom or group which is cleaved during a substitution or displacement reaction. Suitable examples include, but are not limited to halogens, e.g., Br, Cl, I, and sulfonyl esters, such as mesylate, tosylate, triflate, etc.

Typically, the above reaction is done in the presence of a solvent, like a mixture of water and a water miscible organic solvent, wherein the water miscible organic solvent can be a ketone like a C$_1$-C$_3$ ketone, which is understood to be a compound according to the formula R$^a$R$^b$C=O, wherein the R$^a$ and R$^b$ groups are independently selected form C$_1$-C$_3$ alkyl; for example acetone.

The reaction can be performed by combining a solution of ThalP or TsubP with a solution of DMHB to obtain a reaction mixture. The solvent in both solutions can be a water miscible organic solvent which can be the same solvent as described above.

The reaction between the solution of ThalP or TsubP and the solution of DMHB is typically performed in the presence of a base, which can be an inorganic base, such as an alkali metal base, like sodium hydroxide, potassium hydroxide or potassium carbonate The base can be added in a form of an aqueous solution, which is combined with a solution of DMHB in a water miscible organic solvent, thus forming a first mixture. The first mixture is then combined with the solution of ThalP or TsubP and the reaction mixture is formed.

The first mixture can be maintained prior to the combination with the solution of ThalP or TsubP. Maintaining can be done with stirring, at a temperature of about room temperature, for a period of about 5 minutes to about 10 minutes.

The solution of ThalP or TsubP can be cooled prior to combining it with the solution of DMHB. Suitable cooling temperatures can be about 3° C. to about 5° C.

The reaction mixture can then be maintained, leading to the formation of ETHER, C-2 ETHER isomer or a mixture thereof. Maintaining can be done with stirring, at a temperature of about 3° C. to about 5° C., and then at a temperature of about 30° C., for a period of about 5 hours.

The above process can further comprise the recovery of ETHER, C-2 ETHER or a mixture thereof from the reaction mixture, and providing them in a crystalline form.

Figure 3:
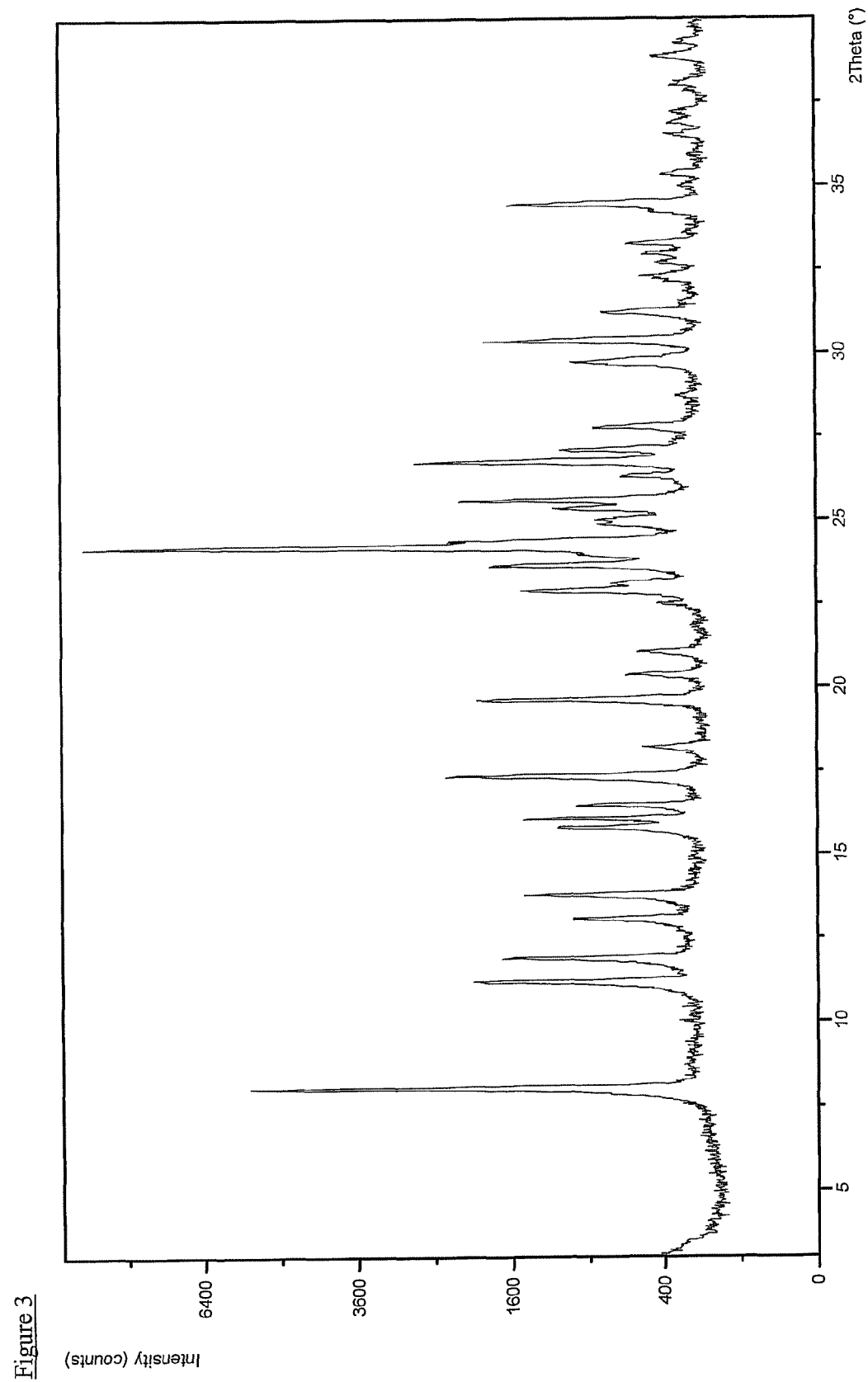
FIG. 3 illustrates a PXRD pattern of a crystalline form of a mixture of 4-(2,6-dichloropyrimidin-4-yloxy)-3,5-dimethylbenzonitrile ("ETHER") and 4-(4,6-dichloropyrimidin-2-yloxy)-3,5-dimethylbenzonitrile ("ETHER C-2 isomer").

For example, a crystalline form of a mixture of ETHER and C-2 ETHER can be characterized by data selected from a group consisting of: a PXRD pattern having peaks at about 8.0, 11.2, 13.1, 13.8 and 24.2±0.2 degrees two-theta; a PXRD pattern as depicted in FIG. 3; and combinations thereof.

The above crystalline form can be further characterized by a PXRD pattern having additional peaks at about 11.9, 17.4, 19.6, 26.7 and 30.4±0.2 degrees two-theta.

The recovery of ETHER, C-2 ETHER or their mixture can comprise, for example, adding water to the reaction mixture, filtering the thus-precipitated solid compound, washing and drying.

Washing can be done with water.

Drying can be done under vacuum, at a temperature such as about 50° C., for a period of about 4 hours.

ETHER or its mixture with C-2 ETHER isomer and their salts can be used to prepare Etravirine and salts thereof, for example by converting ETHER or its mixture with C-2 ETHER isomer or their salt to 4-(6-chloro-2-(4-cyanophenylamino)pyrimidin-4-yloxy)-3,5-dimethylbenzonitrile ("ARCPBN") and subsequently converting ARCPBN to DEBETV and then to ETV and salts thereof.

The conversion of ETHER to ARCPBN of the following formula:

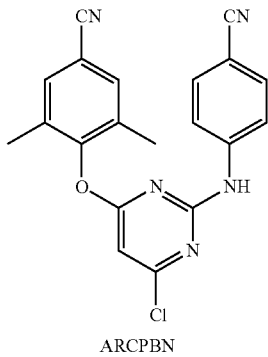
ARCPBN can be done by reacting ETHER or salt thereof and 4-aminobenzonitrile (ABN) of the following formula:

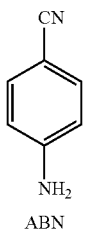
ABN

Typically, the above reaction is done in the presence of a solvent.

Example for suitable solvents can be a can be a polar organic solvents and dipolar aprotic organic solvent, for example, dimethyl sulfoxide ("DMSO"), methylpyrrolidone; an amide, such as dimethylacetamide (DMA), N-methyl-2-pyrrolidone (NMP), dimethylformamide (DMF), 2-pyrrolidone, 1,3-dimethyl-2-imidazolidinone (DMI), imidazolinone; sulfoxides, such as methylsulfonylmethane (MSM) and dimethylsulfate; ketones, like methyl isobutyl ketone (MIBK); or ethers, like tetrahydrofuran (THF).

The reaction can be done by suspending ETHER and a base in the solvent and combining the obtained suspension with a solution of ABN in a dipolar aprotic organic solvent to obtain a reaction mixture comprising ARCPBN.

The base is inorganic base, like alkali metal hydride, such as sodium hydride; lithium diisopropylamide (LDA) or sodium methoxide.

The dipolar aprotic organic solvent in the suspension of ETHER can be the same as in the solution of ABN.

The suspension of ETHER and the base can be formed under nitrogen, for example at a temperature of about room temperature.

After the suspension of ETHER and the base is formed it can be cooled prior to combining it with the solution of ABN, e.g., to a temperature of about 5° C. to about 10° C.

The suspension comprising ETHER and the base can be further maintained, for example with stirring, at a temperature of about 5° C. to about 10° C., for a period of about 10 minutes to about 15 minutes.

The reaction mixture obtained after combining the suspension of ETHER and the base and the solution of ABN can then be maintained. Maintaining the reaction mixture can be done with stirring, at a temperature of about 5° C. to about 10° C., for a period of about 45 minutes to about 75 minutes.

ARCPBN can be recovered from the reaction mixture. The recovery can comprise, for example, extracting ARCPBN from the reaction mixture, concentrating the extract to obtain a precipitate which can be filtered, washed and dried.

The extraction can comprise cooling the reaction mixture, adding water, which can be salted water, i.e., brine; and organic solvent which can be, for example, an ester, such as ethylacetate (EtOAc), to obtain an aqueous phase and an organic phase; and isolating ARCPBN from the organic phase.

Washing can be done with an organic solvent, which can be the same as in the previous extraction step, e.g., EtOAc.

Drying can be done under vacuum, at a temperature such as about 50° C., for a period of about 4 hours.

The obtained ARCPBN can than be purified, if desired. The purification process can comprise crystallizing ARCPBN from a mixture comprising tetrahydrofuran (THF) as a solvent, and a mixture of ethanol and water as an anti-solvent.

Typically, the crystallization comprises providing a solution ARCPBN in THF and combining said solution with a mixture of ethanol and water to obtain a suspension comprising purified ARCPBN. The solution can be provided by combining ARCPBN and THF. The solution can then be cooled, prior to combining it with the mixture of ethanol and water, to a temperature such as about 5° C. The ratio of ethanol and water in the mixture is about 1:1 (v/v). The addition of the anti-solvent to the solution of ARCPBN in THF is done over a period of about 1 hour, preferably at a temperature of about 5° C. After the suspension is formed, it can be maintained, for example with stirring. Maintaining can be done at a temperature of about 5° C., over a period of about 1 hour.

Figure 4:
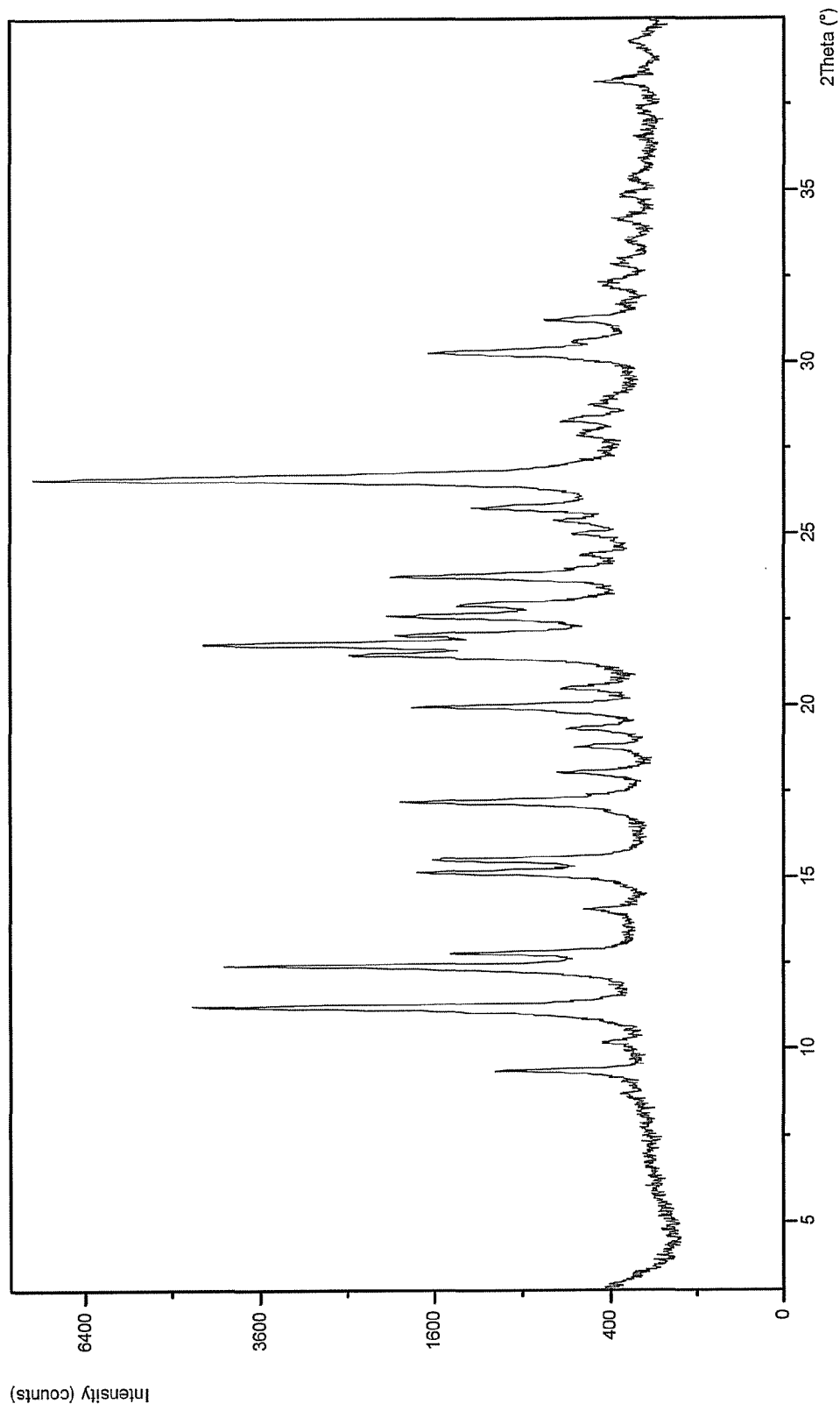
FIG. 4 illustrates a PXRD pattern of crystalline 4-(6-chloro-2-(4-cyanophenylamino)pyrimidin-4-yloxy)-3,5-dimethylbenzonitrile ("ARCPBN").

The above purified ARCPBN can then be recovered from the suspension, for example in a crystalline form that can be characterized by data selected from a group consisting of: a PXRD pattern having peaks at 9.4, 12.4, 15.5, 21.8 and 26.6±0.2 degrees two-theta; a PXRD pattern as depicted in FIG. 4; and combinations thereof.

The above crystalline ARCPBN can be further characterized by a PXRD pattern having additional peaks at 11.3, 15.2, 20.0, 23.8 and 30.3±0.2 degrees two-theta.

The recovery can comprise, for example, filtering the solid compound and drying it.

ARCPBN can be used to prepare Etravirine or a salt thereof via DEBETV (see examples 3-6). The process can comprise reacting ARCPBN and ammonia, preferably in the presence of a base, such as N-methyl-2-pyrrolidone ("NMP") to obtain DEBETV; and brominating the obtained DEBETV, preferably in the presence of a base, such as sodium hydroxide, to obtain Etravirine.

The present invention also describes a process for the purification of the compound of formula I of the following structure:

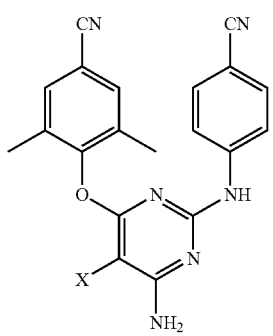

Formula I comprising reacting a salt of the compound of formula I and a base in a mixture of water and a water miscible organic solvent; wherein X is either H or Br. When X is H the water miscible organic solvent is 1-propanol, and when X is Br the water miscible organic solvent is acetone. When X is H, the compound of formula I refers to DEBETV. When X is Br, the compound of formula I refers to Etravirine.

The compound of formula I is preferably obtained in a total purity level of at least 97.9% by HPLC when X is H, and at least 99.79% by HPLC when X is Br, Preferably, the total purity level is about 98.9% by HPLC when X is H, and about 99.96% by HPLC when X is Br.

The starting salt can be formed, for example, by reacting the compound of formula I with an acid. However, in this step only little purification is achieved.

The acid can be, for example, p-toluenesulfonic acid ("PTSA"), nitric acid, phosphoric acid; benzenesulfonic acid or ethanesulfonic acid.

Typically, the reaction of formula I with the acid can be done in the presence of a solvent. The reaction can comprise combining a suspension of the compound I in the organic solvent with the acid, to obtain a second suspension, which typically, contains a precipitate of the salt of compound I.

The acid used in the above reaction can be in a form of a solution, where the solvent in the solution can be the same as in the reaction of compound I and the acid.

The second suspension can be maintained prior to recovering the salt, for example, with stirring, and at a temperature of about room temperature, for a period of about 1 hour.

The recovery of the salt of the compound of formula I can be done, for example, by filtration, providing the salt in a crystalline form.

Figure 6:
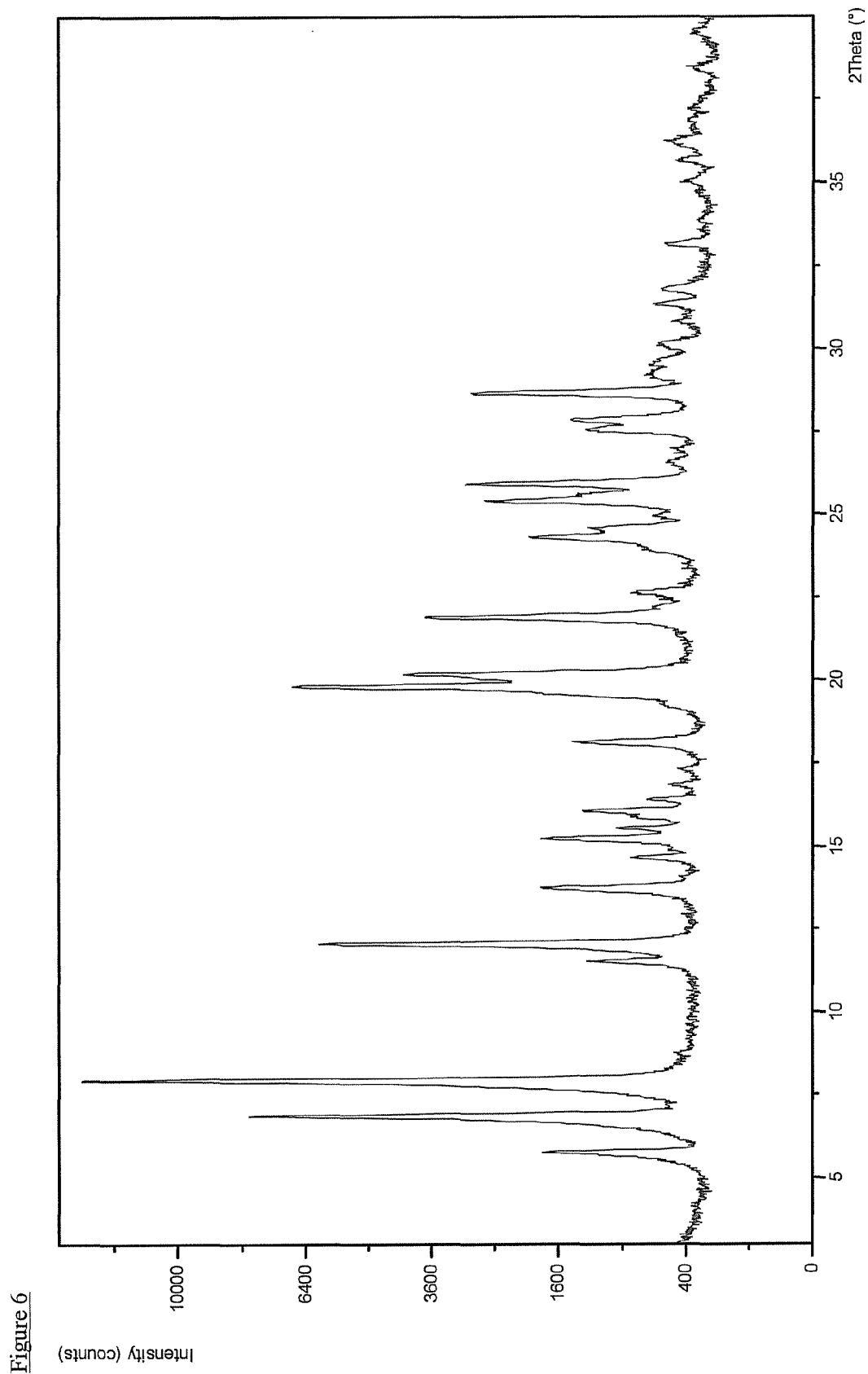
FIG. 6 illustrates a PXRD pattern of crystalline debrometravirine tosylate salt ("DEBETV-Ts").

When X is H, i.e., crystalline debrometravirine tosylate salt ("DEBETV-Ts") is obtained and can be characterized by data selected from a group consisting of at least one of: a PXRD pattern having peaks at about 5.8, 6.9, 8.0, 12.1 and 19.8±0.2 degrees two-theta; a PXRD pattern as depicted in FIG. 6; and combinations thereof. The above crystalline DEBETV-Ts form can be further characterized by a PXRD pattern having additional peaks at about 13.8, 18.1, 21.9, 25.9 and 28.6±0.2 degrees two-theta.

Figure 7:
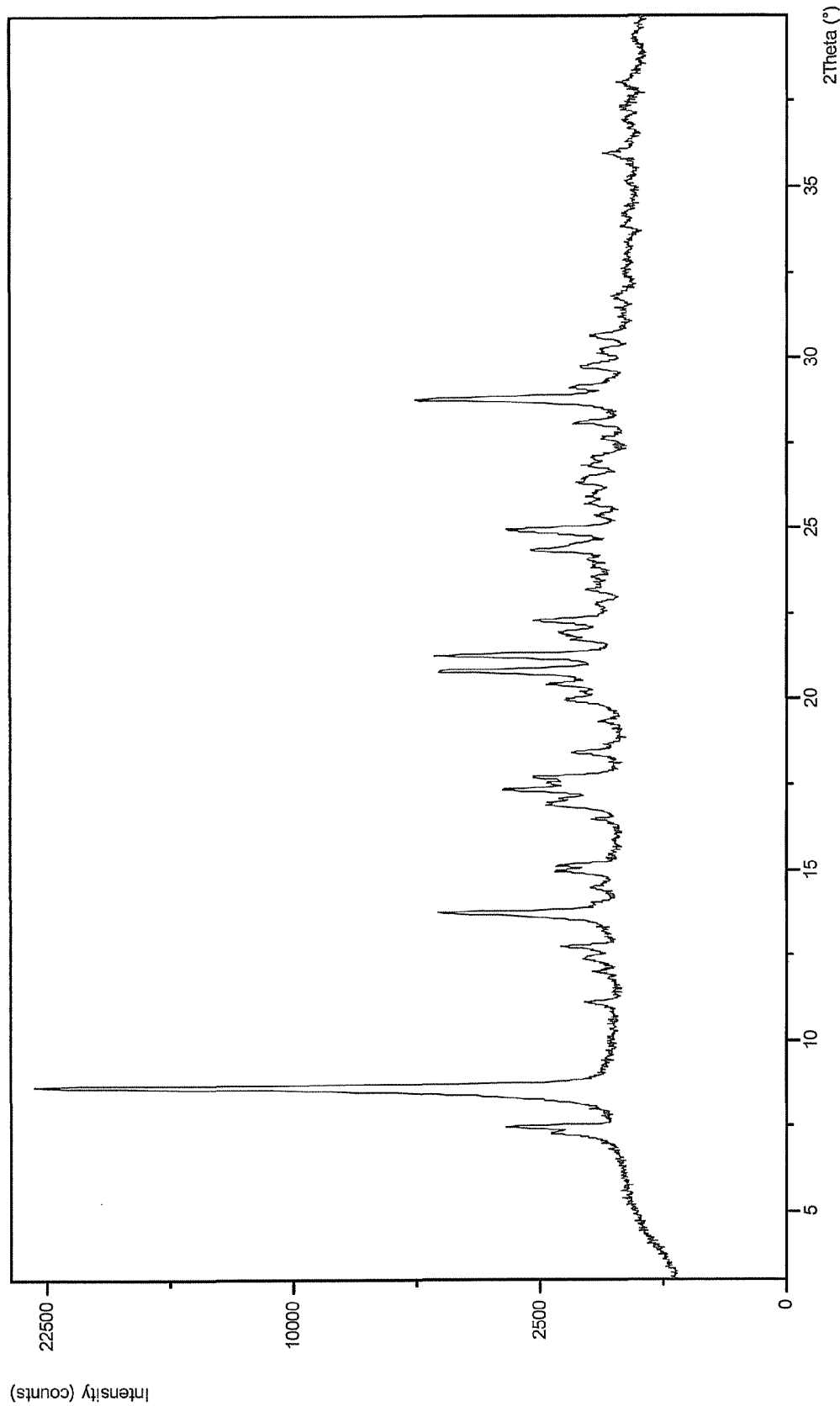
FIG. 7 illustrates a PXRD pattern of crystalline Etravirine tosylate salt ("ETV-Ts").

When X is Br, i.e., crystalline Etravirine tosylate salt ("ETV-TS") is obtained and can be characterized by data selected from a group consisting of at least one of: a PXRD pattern having peaks at about 8.7, 13.8, 20.8, 25.0 and 28.8±0.2 degrees two-theta; a PXRD pattern as depicted in FIG. 7; and combinations thereof. The above crystalline ETV-TS form can be further characterized by a PXRD pattern having additional peaks at about 7.5, 12.8, 17.4, 18.4 and 22.3±0.2 degrees two-theta.

The present invention also describes nitrate, phosphate, benzesulphonate and ethanesulfonate salts of Etravirine, which can be prepared by the process described in examples 12-15, and can be obtained in crystalline forms.

Figure 8:
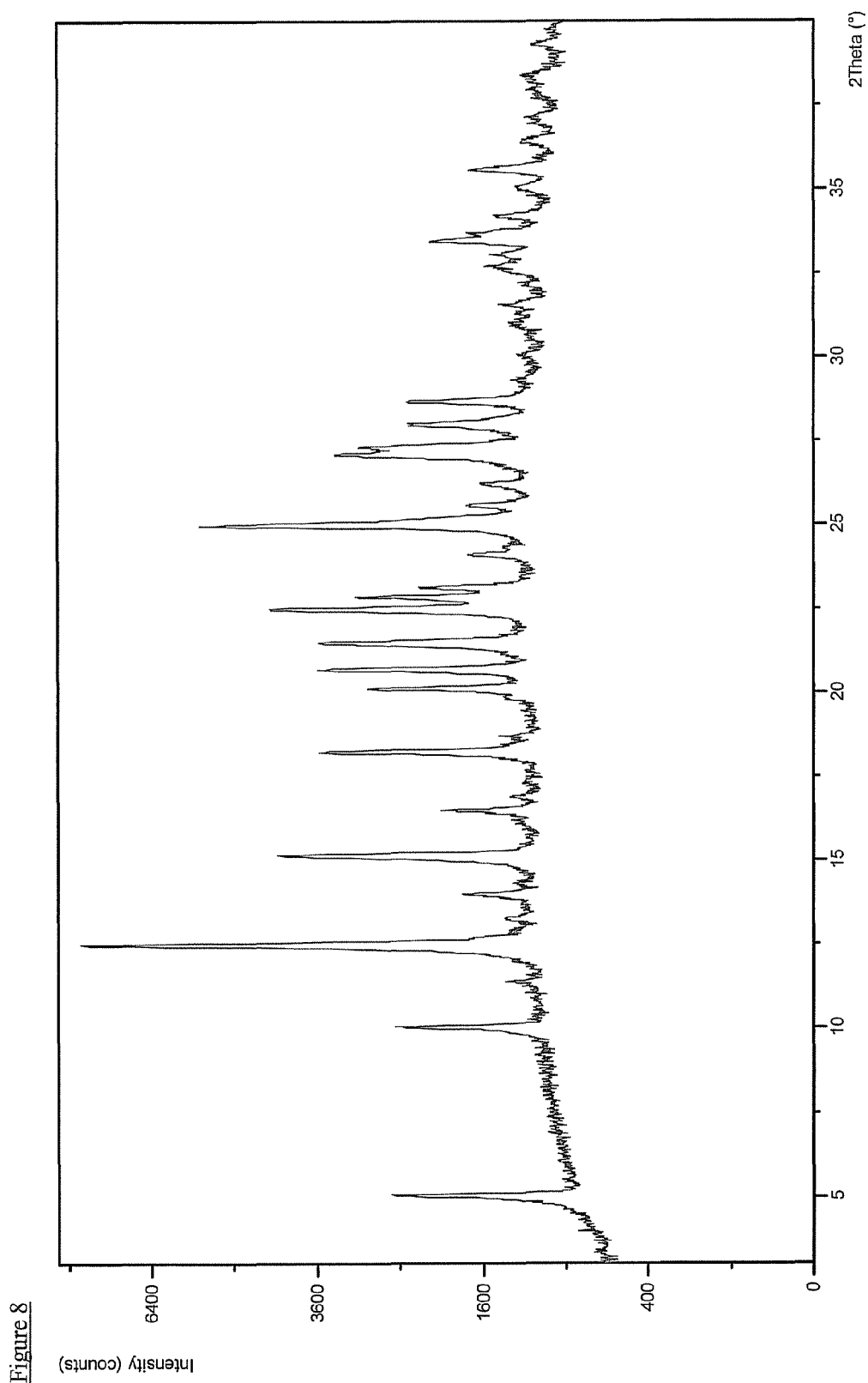
FIG. 8 illustrates a PXRD pattern of crystalline Etravirine nitrate salt ("ETV-NT").

Crystalline Etravirine nitrate salt ("ETV-NT") can be characterized by data selected from: a PXRD pattern having peaks at about 5.1, 10.1, 12.5, 20.1 and 25.0±0.2 degrees two-theta; a PXRD pattern as depicted in FIG. 8; and combinations thereof. The above crystalline ETV-NT salt can be further characterized by a PXRD pattern having additional peaks at about 15.2, 18.2, 21.5, 22.5 and 28.0±0.2 degrees two-theta.

Figure 9:
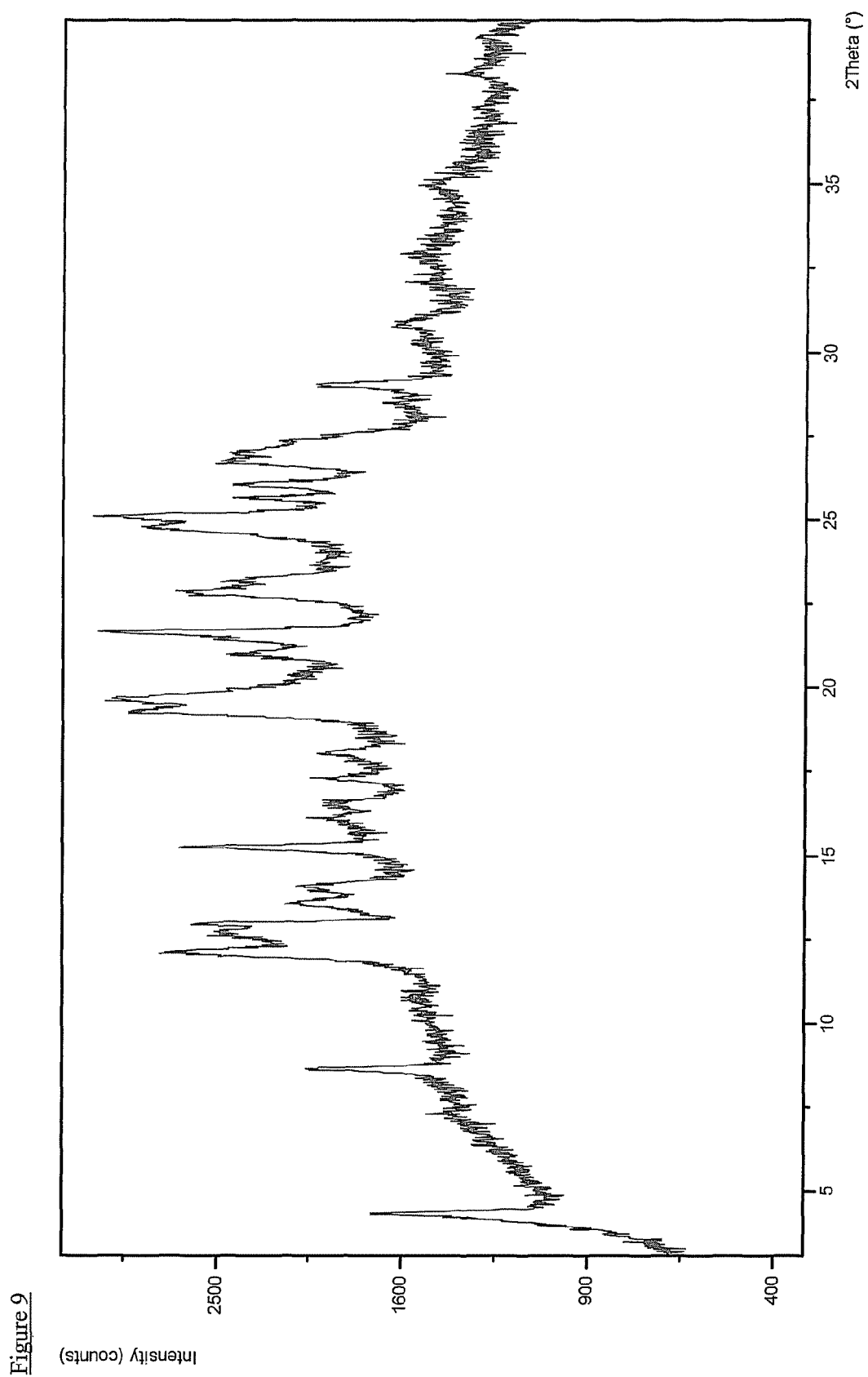
FIG. 9 illustrates a PXRD pattern of crystalline Etravirine phosphate salt ("ETV-PH").

Crystalline Etravirine phosphate salt ("ETV-PH") can be characterized by data selected from: a PXRD pattern having peaks at about 4.3, 8.6, 12.1, 19.7 and 21.7±0.2 degrees two-theta; a PXRD pattern as depicted in FIG. 9; and combinations thereof. The above ETV-PH salt can be further characterized by a PXRD pattern having additional peaks at about 13.0, 15.2, 22.8, 25.1 and 29.0±0.2 degrees two-theta.

Figure 10:
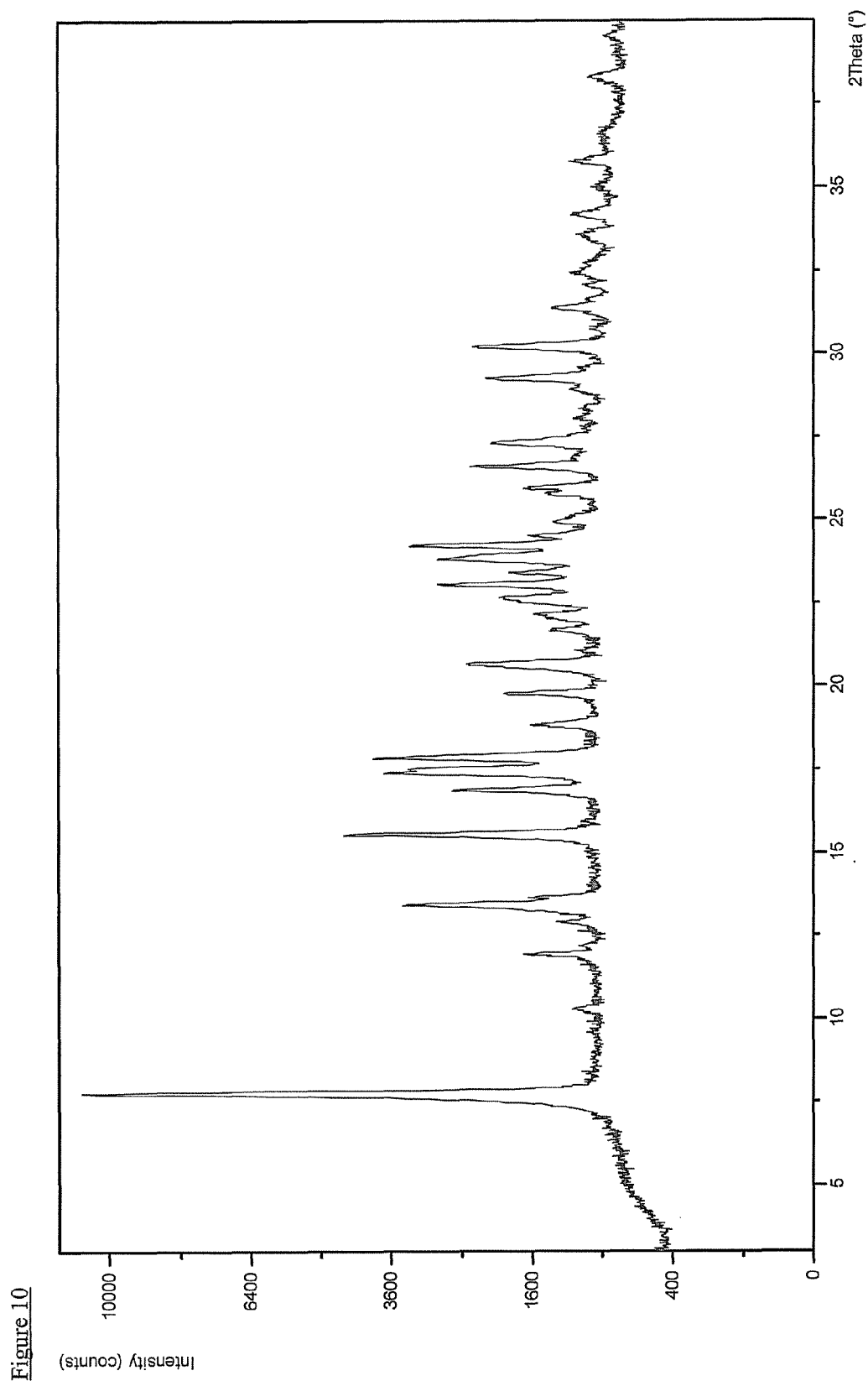
FIG. 10 illustrates a PXRD pattern of crystalline Etravirine benzenesulphonate salt ("ETV-BZ").

Crystalline Etravirine benzesulphonate salt ("ETV-BZ") can be characterized by data selected from at least one of: a PXRD pattern having peaks at about 7.8, 15.5, 16.9, 17.8 and 24.2±0.2 degrees two-theta; a PXRD pattern as depicted in FIG. 10; and combinations thereof. The above crystalline ETV-BZ salt can be further characterized by a PXRD pattern having additional peaks at about 13.4, 17.5, 20.7, 23.0 and 30.2±0.2 degrees two-theta.

Figure 11:
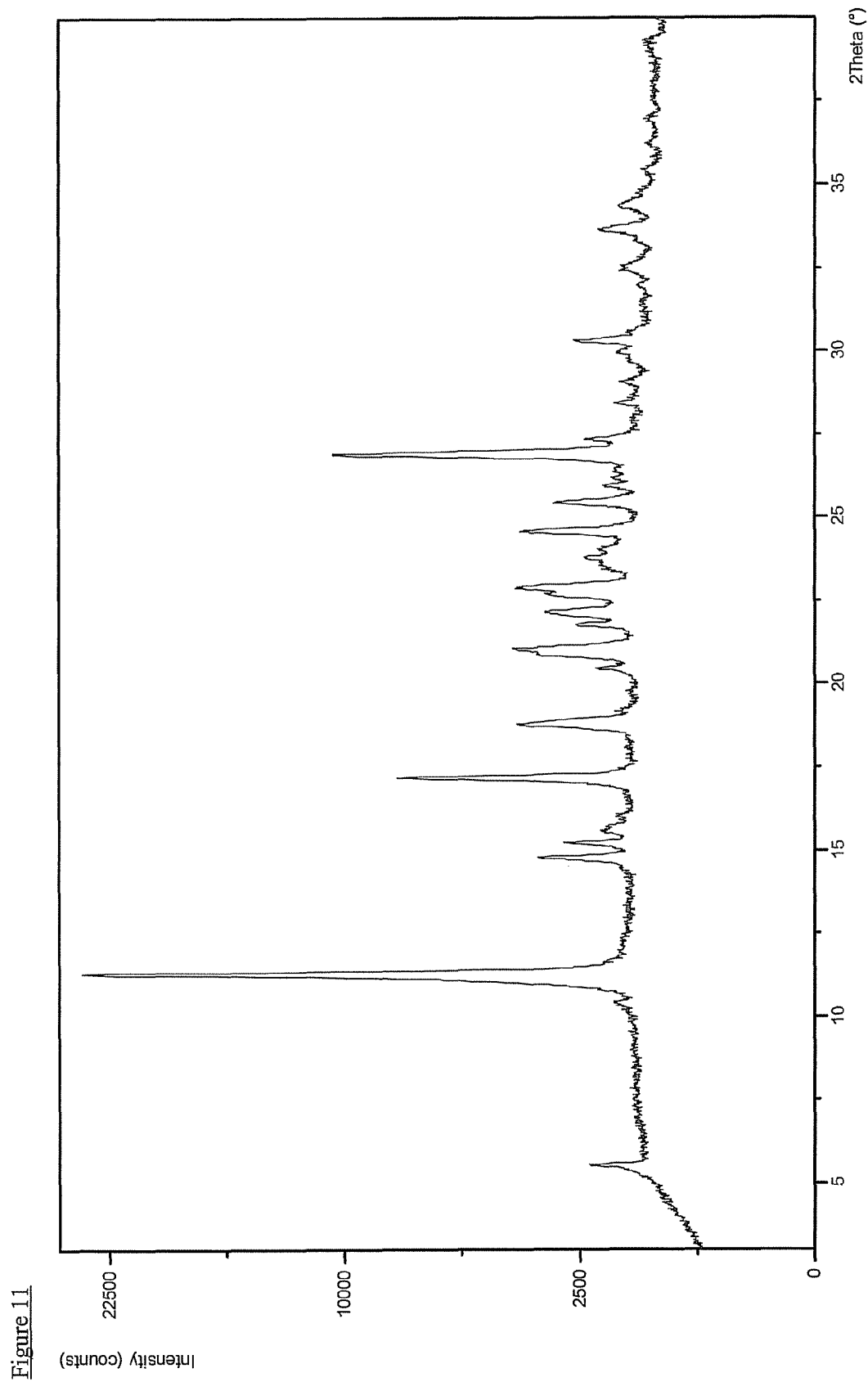
FIG. 11 illustrates a PXRD pattern of crystalline Etravirine ethanesulfonate salt ("ETV-ES").

Crystalline Etravirine ethanesulfonate salt ("ETV-ES") can be characterized by data selected from at least one of a PXRD pattern having peaks at about 5.6, 11.3, 14.8, 17.2 and 26.9±0.2 degrees two-theta; a PXRD pattern as depicted in FIG. 11; and combinations thereof. The above crystalline ETV-ES salt can be further characterized by a PXRD pattern having additional peaks at about 18.9, 22.9, 24.6, 25.4 and 30.3±0.2 degrees two-theta.

The compound of formula I is purified by reacting its salt, either isolated or not, with a base. The salt of the compound of formula I can be suspended in a water miscible organic solvent, and a base is added to the suspension. The water miscible organic solvent can be, for example, the same as in the previous step or a different one. The base that is reacted with the compound of formula I can be an inorganic base, such as an alkali metal base, like an alkali metal hydroxide, e.g., sodium hydroxide.

The addition of the base transforms the salt of the compound of formula I to its free base form, which in the case of Etravirine is soluble for a very short period of time, i.e., a solution is formed for a very short period of time. Further, the salt precipitates spontaneously and the solution transforms to a suspension. In the case of DEBETV, a suspension containing a precipitate of DEBETV is obtained.

The suspension can then be maintained prior to the recovery of the purified compound of formula I. Maintaining can be done with stirring, for example, at a temperature of about room temperature, for a period of about 30 minutes.

To ensure complete precipitation, an anti-solvent, such as water, can be added, fowling a reaction mixture, which can be further maintained prior to recovering the compound of formula I. Maintaining can be done with stirring, for example, at a temperature of 0° C. to about 5° C., for a period of about 1 hour.

The above process can further comprise the recovery of the purified compound of formula I from the suspension. The recovery can be done, for example, by filtering the solid compound and drying. The drying can be done under vacuum, at a temperature such as about 50° C., for a period of about 5 hours.

The obtained purified compound of formula I wherein X is H (i.e., DEBETV), can be in a crystalline form.

Figure 5:
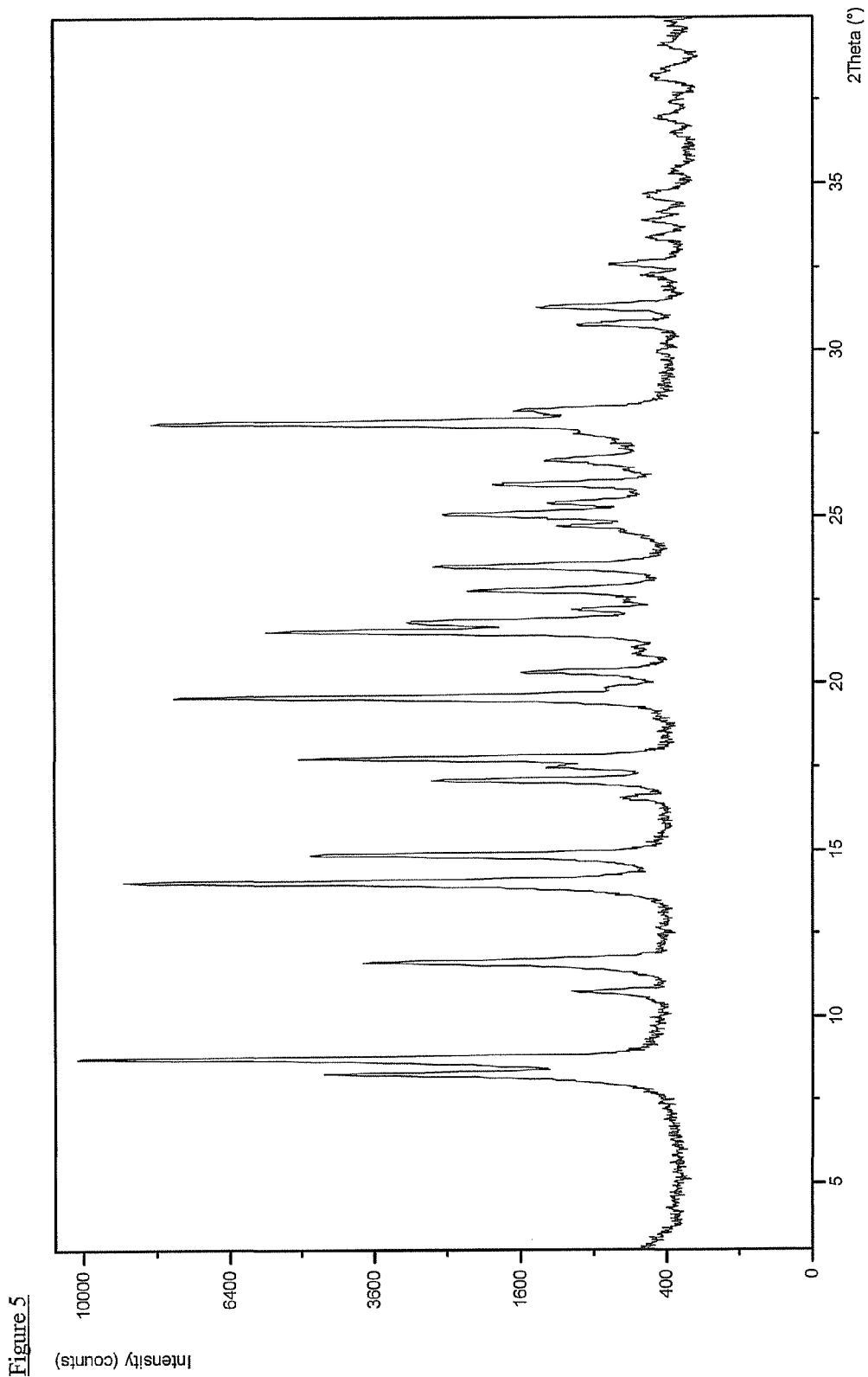
FIG. 5 illustrates a PXRD pattern of crystalline debrometravirine ("DEBETV").

The above crystalline debrometravirine ("DEBETV") can be characterized by data selected from: a PXRD pattern having peaks at 8.3, 8.8, 11.6, 17.8 and 23.5±0.2 degrees two-theta; a PXRD pattern as depicted in FIG. 5; and combinations thereof. The above crystalline DEBETV can be further characterized by a PXRD pattern having additional peaks at 10.7, 14.0, 14.9, 19.6 and 27.5±0.2 degrees two-theta.

The obtained purified compound of formula I wherein X is H (i.e., DEBETV), can then be used to prepare Etravirine and salts thereof.

The conversion of DEBETV, (i.e., X=H) to Etravirine (i.e., X=Br) can be done, for example, by reacting the compound with bromine to obtain Etravirine (for example see examples 5-6)

Experimental:
PXRD Method

Samples, after being powdered in a mortar and pestle, were applied directly on silicon plate holders. The X-ray powder diffraction pattern was measured with Philips X'Pert PRO X-ray powder diffractometer, equipped with Cu irradiation source=1.54184 ´ ( ngström), X'Celerator (2.022° 2Q) detector. Scanning parameters: angle range: 3-40 deg., step size 0.0167, time per step 37 s, continuous scan.

NMR Method of Analysis

One-dimensional ($^1$H, $^{13}$C-APT) spectra of the sample were recorded at the Center for Nuclear Magnetic Resonance Spectroscopy, Ruđer Bošković Institute, Zagreb, Croatia on a Bruker Avarice DRX 600 NMR spectrometer operating at 600.1 and 150.9 MHz. Deuterated dimethylsulfoxide (DMSO-d6) was used as a solvent.

EXAMPLES

Example 1

Preparation of 4-(2,6-dichloropyrimidin-4-yloxy)-3,5-dimethylbenzonitrile (ETHER)

2,4,6-Trichloropyrimidine (TCP) (100 g, 545 mmol) was dissolved in 300 mL of acetone and cooled to 3-5° C. with stirring using mechanical stirrer in a 2-L reactor.

A solution of 4-hydroxy-3,5-dimethylbenzonitrile (DMHB) (80.23 g 545 mmol) in 450 mL of acetone was prepared in an Erlenmeyer flask. In a separate Erlenmeyer flask, a solution of 22.89 g (573 mmol) of NaOH in 250 mL of water was prepared. The solution of DMHB in acetone was added with stirring into the previously made solution of NaOH in water. The resulting mixture was stirred at room temperature for 5-10 minutes and then added dropwise at 3-5° C. to the previously cooled solution of TCP in acetone.

The reaction mixture was stirred at 3-5° C. for 1 hour, and then at 30° C. for a further 4 hours. The reaction mixture was then cooled down to room temperature, 500 mL of water was added and the mixture was stirred for 5 minutes. A solid precipitated and was separated by filtration. The filtered solid was washed with 3×650 mL of water and then dried under vacuum at 50° C. for 4 hours.

Yield: 155 g (97%) of the mixture of 4-(2,6-dichloropyrimidin-4-yloxy)-3,5-dimethylbenzonitrile ('ETHER') and 4-(4,6-dichloropyrimidin-2-yloxy)-3,5-dimethylbenzonitrile ('C-2 isomer') in a ratio of 87.43:11.62.

$^1$H NMR (600.1 MHz, DMSO-d$_6$, 50° C.), δ/ppm: 7.75 (<1H, s, H5 of C-2 isomer), 7.69 (>2H, br, E19, H11 of ether and C-2 isomer), 7.52 (1H, s, H5 of ether), 2.12 (>6H, s, H14, H15 of ether and C-2 isomer).

$^{13}$C NMR (150.9 MHz, DMSO-d$_6$, 50° C.), δ/ppm: 169.9 (C4 of ether and C2 of C-2 isomer?), 163.6 (C4, C6 of C-2 isomer), 162.7 (C6 of ether), 159.1 (C2 of ether), 152.6 (C7 of ether and C-2 isomer), 133.3 (C9, C11 of ether), 133.2 (C9, C11 of C-2 isomer), 132.8 (C8, C12 of ether), 132.7 (C8, C12 of C-2 isomer), 118.7 (C13 of C-2 isomer), 118.7 (C13 of ether), 117.3 (C5 of C-2 isomer), 109.9 (C10 of ether and C-2 isomer), 107.1 (C5 of ether), 16.1 (C14, C15 of ether and C-2 isomer).

Example 2

Preparation of 4-(6-chloro-2-(4-cyanophenylamino) pyrimidin-4-yloxy)-3,5-dimethylbenzonitrile ("ARCPBN")

A portion of the mixture of ETHER and C-2 isomer prepared in Example 1 (20 g, 68.00 mmol) was suspended under nitrogen in 200 mL of DMA in a 2-L reactor by stirring with a mechanical stirrer at room temperature. The suspension was cooled down to +10° C. To the resulting mixture was added NaH (6.8 g, 178.5 mmol of 60% suspension in mineral oil) and the resulting reaction mixture was stirred at +10° C. for 10 minutes.

A solution of 4-aminobenzonitrile (ABN) (8 g, 71.4 mmol) in 100 mL of DMA was prepared in a 250 mL Erlenmeyer flask, and transferred to a dropping funnel. and was added dropwise to the reaction mixture over 1 hour at +10° C. After the ABN addition was complete, the resulting reaction mixture was stirred at +10° C. for at least 1 more hour. It was then cooled down to 0-5° C. and 500 mL of EtOAc was added. To this resulting mixture was added 150 mL of water dropwise, together with 10 mL of saturated NaCl. The thus obtained solution was stirred for 10 minutes, and the layers were separated. The water layer was extracted with 500 mL of EtOAc and layers were separated. The organic layers were collected and washed with 400 mL of saturated NaCl and 2×400 mL of diluted NaCl (saturated NaCl:water 1:1).

The organic layer was concentrated to a volume of about 250 mL (8% in respect to starting ether), stirred at room temperature for 2 h and filtered. The filtered solid was washed with EtOAc (2×40 mL), and dried under vacuum for 4 h at 50° C.

Yield of crude ARCPBN: 13.72 g (53.69%) HPLC purity: 95 area %

The crude ARCPBN was dissolved in 256 mL of THF. The solution was cooled down to 5° C., and 388 mL of a mixture of tech. EtOH:water 1:1 was added dropwise over 1 hour at 5° C. to form a suspension. The obtained suspension was stirred for 1 hour at 5° C., and the precipitated solid was filtered and dried in vacuo for 4 h at 50° C.

Yield of purified ARCPBN: 12.64 g (92.13%); PXRD depicted in FIG. 4; HPLC purity: 98.7 area %

Example 3

Preparation of Debrometravirine (DEBETV)

The purified ARCPBN (31.14 g, 82.86 mmol) was dissolved in 250 mL of NMP at room temperature in a 600-mL autoclave. $NH_3$ (125 mL, 1.65 mol of a 25% water solution) was added to the solution to form a reaction mixture. The reaction mixture was heated to 120° C. and stirred for 20 h at 120° C. to form a solution. The obtained solution was then cooled down to room temperature and 200 mL of water were added dropwise. The resulting mixture was then cooled to 0-5° C. and stirred for an additional 2 h. A solid precipitate formed and was separated by filtration and dried under vacuum for 5 h at 50° C.

Yield of crude DEBETV: 26.04 g (88.2%). HPLC purity: 94.7 area %

Example 4

Preparation of Debrometravirine (DEBETV)

Purified ARCPBN (30 g, 79.83 mmol) was dissolved in 241 mL of NMP at room temperature in a 600-mL autoclave. $NH_3$ (120 mL, 1.59 mol of a 25% water solution) was added to the solution. The resulting reaction mixture was heated to 120° C. and stirred for 19 h at 120° C. to form a solution. The obtained solution was then cooled down to room temperature and 200 mL of water was added dropwise. The resulting mixture was then cooled to 0-5° C. and stirred for an additional 2 h. A solid precipitate formed and was separated by filtration and dried in vacuo for 5 h at 50° C. Yield of crude DEBETV: 25.61 g (90.0%). HPLC purity: 95.1 area %

Example 5

Preparation of Etravirine

Purified DEBETV (8.9 g, 24.97 mmol) was suspended in 445 mL of 1-propanol in a 1 L flask with mechanical stirring, and the suspension was then cooled to +5° C.

Bromine (1.29 mL, 24.97 mmol) was added dropwise at 5-10° C. The resulting reaction mixture was stirred at +10° C. for 30 minutes, and then another 1.29 mL (24.97 mmol) of bromine was added dropwise at 10° C. The resulting reaction mixture was stirred at +10° C. for 30 minutes and then at room temperature for 2 hours. Then water (89 mL) was added to the mixture and 10% aqueous NaOH (9.18 mL, 44.95 mmol) was added dropwise to form a suspension. The suspension was stirred for 1 h at room temperature and then for 1 h at 0-5° C. A solid precipitate was separated by filtration and washed with 178 mL of an ice-cold mixture of 1-propanol:water (1:1). The filtered solid was dried under vacuum for 4 h at 50° C. Yield of crude ETV: 10.09 g (92.82%) HPLC purity: 99.4%.

Example 6

Preparation of Etravirine

Puffed DEBETV (21.39 g, 60.01 mmol) was suspended in 1.06 L of 1-propanol in a 2 L flask with mechanical stirring and the suspension was then cooled to +5° C. Bromine (3.10 mL, 60.05 mmol) was then added dropwise at 5-10° C. The resulting reaction mixture was stirred at +10° C. for 30 minutes, and then another 3.10 mL (60.05 mmol) of bromine was added dropwise at 10° C. The resulting reaction mixture was stirred at +10° C. for 30 minutes and then at room temperature for 2 hours. Water (214 mL) was then added to the mixture and 10% aqueous NaOH (22.1 mL, 107.96 mmol) was then added dropwise The suspension was stirred for 1 h at room temperature and then for 1 h at 0-5° C. A solid precipitate was separated by filtration and washed with 428 mL of an ice cold mixture of 1-propanol: water (1:1). The filtered solid was dried in vacuo for 4 h at 50° C.

Yield of crude ETV: 23.49 g (89.90%). HPLC purity: 99.1 area %

Example 7

Purification of Debrometravirine (DEBETV)

Crude DEBETV was suspended in 651 mL of 1-PrOH in a 1 L flask with mechanical stirring at room temperature to form a suspension.

p-TsOH×$H_2O$ (15.29 g, 80.38 mmol, dissolved in 130 mL of 1-PrOH) was slowly added to the suspension. The resulting suspension was stirred at room temperature for 1 h. A solid precipitate formed and was separated by filtration. The product, crystalline DEBETV tosylate salt was obtained and characterized by PXRD as shown in FIG. 6.

The solid was suspended in 521 mL of 1-PrOH, and 10% aqueous NaOH (31.6 mL, (87.69 mmol) was added dropwise. The suspension was stirred for 30 minutes at room temperature. Then, 130 mL of water was added and the resulting mixture was stirred for 1 h at 0-5° C. A solid precipitate was separated by filtration and dried under vacuum for 5 h at 50° C. The product, crystalline DEBETV, was characterized by PXRD as shown in FIG. 5. Yield of purified DEBETV: 81.1% (21.11 g); HPLC purity: 98.6 area %.

Example 8

Purification of Debrometravirine (DEBETV)

Crude DEBETV (25.61 g; HPLC purity 95.1 area %) was suspended in 640 mL of 1-PrOH at room temperature. p-TsOH×$H_2O$ (15.04 g, 79.01 mmol) was dissolved in 128 mL of 1-PrOH, and the solution was added slowly into the DEBETV suspension. The suspension was stirred at room temp. for 1 h. A solid precipitate was separated by filtration. The obtained produce, crystalline DEBETV tosylate salt, was characterized by PXRD as shown in FIG. 6.

The solid product was then suspended in 1-PrOH (512 mL) and 10% aqueous NaOH (31.08 mL, 86.20 mmol) was added dropwise. The suspension was stirred for 30 minutes at room temperature. Then, 128 mL of water was added and resulting mixture was stirred for 1 h at 0-5° C. A solid precipitate was separated by filtration and dried in vacuo for 5 h at 50° C.

The obtained product, crystalline DEBETV, was characterized by PXRD as shown in FIG. 5. Yield of purified DEBETV: 83.5% (21.39 g); HPLC purity: 97.9 area %.

Example 9

Purification of Debrometravirine (DEBETV)

Crude DEBETV (2 g; HPLC purity 94.4 area %) was suspended in 15 mL of acetone at room temperature. p-TsOH×$H_2O$ (1.18 g, 6.17 mmol dissolved in 5 mL of acetone) was added slowly into the DEBETV suspension. The suspension was stirred at room temp. for 1 h and the solid precipitate was then separated by filtration. The obtained product, crystalline DEBETV tosylate salt was characterized by PXRD as shown in FIG. 6.

The solid product was suspended in 10 mL of acetone and 1.77 mL (4.90 mmol) of 10% NaOH was added dropwise. The suspension was stirred for 30 minutes at room temp. Then 5 mL of water was added and the resulting mixture was stirred for 1 h at 0-5° C. A solid precipitate was separated by filtration and air dried overnight.

The obtained crystalline DEBETV product was characterized by PXRD as shown in FIG. 5. Yield of purified DEBETV: 66.3% (66.3 g); HPLC purity: 98.9 area %.

Example 10

Purification of Etravirine Via PTSA Salt

Crude ETV was suspended in 252 mL of acetone at room temperature and 4.85 g (25.50 mmol) of p-TsOH×$H_2$O (dissolved in 50.5 mL acetone) was added slowly. The resulting mixture was stirred at room temperature for 1 h and a solid precipitate formed thereby was then separated by filtration. Crystalline Etravirine tosylate salt characterized by PXRD as shown in FIG. 7 was obtained.
The Crystalline Etravirine tosylate was suspended in 252 mL of acetone and 10.04 mL (27.82 mmol) of 10% aqueous NaOH was then added dropwise to form a suspension. The suspension was stirred for 30 minutes at room temperature. Then, 50.5 mL of water was added, whereupon the mixture dissolved and immediately started to crystallize, The resulting mixture was then stirred for 1 h at 0-5° C. The precipitated solid was separated by filtration and dried under vacuum for 5 h at 50° C. Yield of purified ETV: 6.83 g (67.7%); HPLC purity: 99.96 area %.

Example 11

Purification of Etravirine Via PTSA Salt

Crude ETV (5 g) was suspended in 125 mL of acetone at room temperature and p-TsOH×$H_2$O (2.40 g, 12.64 mmol, dissolved in 25 mL of acetone) was added slowly. The resulting mixture was stirred at room temperature for 1 h and the resulting solid precipitate was separated by filtration. The obtained crystalline Etravirine tosylate salt was characterized by PXRD as shown in FIG. 7.

The solid product was then suspended in 150 mL of acetone and 4.89 mL (13.55 mmol) of 10% aqueous NaOH was added dropwise. The resulting suspension was stirred for 30 minutes at room temperature. Then 60 mL of water was added portionwise. The mixture formed a solution, but then immediately began to crystallize. The mixture was stirred for 1 h at 0-5° C. The solid was separated by filtration and air dried overnight. Yield of purified ETV: 4.41 g (88.2%); HPLC purity: 99.76 area %

Example 12

Purification of Etravirine Via Nitrate Salt

Crude ETV (500 mg; 1.15 mmol) was suspended in 12.5 mL of acetone at room temperature. Nitric acid (65%, 87.5 µL, 1.1 eq) was dissolved in 2.5 mL of acetone and added slowly to provide a reaction mixture. The reaction mixture was stirred at room temperature for 1 h and a solid precipitate formed and was separated by filtration. The obtained crystalline Etravirine nitrate salt was characterized by PXRD as shown in FIG. 8.

The obtained solid was suspended in 12.5 mL of acetone and 0.5 mL (1.2 eq) of 10% aqueous NaOH was added dropwise to form a suspension. The suspension was stirred for 30 minutes at room temperature, and then 2.5 mL of water was added to provide a solution. The solution was stirred for 30 min at 0-5° C., and then an additional 2.5 mL of water was added. A crystalline precipitate began to form. The mixture was stirred for 1 h at 0-5° C. and the precipitated crystalline solid was separated by filtration and dried under vacuum for 5 h at 50° C. Yield of purified ETV: 250 mg (50%); HPLC purity: 99.82 area %

Example 13

Purification of Etravirine Via Phosphate Salt

Crude ETV (500 mg; 1.15 mmol) was suspended in 12.5 mL of acetone at room temperature and 85.22 µL (1.1 eq) of phosphoric acid (85%, dissolved in 2.5 mL of acetone) was added slowly to produce a reaction mixture. The reaction mixture was stirred at room temperature for 1 h and a solid precipitate formed and was separated by filtration. The thus obtained semi crystalline Etravirine phosphate salt was characterized by PXRD as shown in FIG. 9.

The product was suspended in 12.5 mL of acetone and 0.5 mL (1.2 eq) of 10% aqueous NaOH was added dropwise to form a suspension. The suspension was stirred for 30 minutes at room temperature. Then 2.5 mL of water was added to form a solution. The solution was stirred for 30 min at 0-5° C., and then an additional 2.5 mL of water was added, whereupon crystals began to form. The resulting mixture was stirred for 1 h at 0-5° C. A solid precipitate formed and was separated by filtration and dried under vacuum for 5 h at 50° C. Yield of purified ETV: 430 mg (86%); HPLC purity: 99.79 area %.

Example 14

Purification of Etravirine Via Benzenesulphonate Salt

Crude ETV (500 mg; 1.15 mmol) was suspended in 12.5 mL of acetone at room temperature. Benzenesulfonic acid (200 mg; 1.1 eq, dissolved in 2.5 mL of acetone) was added slowly to produce a reaction mixture. The reaction mixture was stirred at room temperature for 1 h and a solid precipitate formed and was separated by filtration. The thus obtained crystalline Etravirine benzenesulphonate salt was characterized by PXRD as shown in FIG. 10.

The solid product was then suspended in 12.5 mL of acetone. 10% Aqueous NaOH (0.5 mL, 1.2 eq) was then added dropwise. The resulting suspension was stirred for 30 minutes at room temperature, and then 2.5 mL of water was added. The solid then dissolved and immediately began to crystallize. The resulting mixture was stirred for 1 h at 0-5° C. The crystalline solid was separated by filtration and dried under vacuum for 5 h at 50° C. Yield of purified ETV=370 mg (74%); HPLC purity: 99.82 area %.

Example 15

Purification of Etravirine Via Ethanesulfonate Salt

Crude ETV (500 mg; 1.15 mmol) was suspended in 12.5 mL of acetone at room temperature. Ethanesulfonic acid (70% water solution, 148 µL; 1.1 eq; dissolved in 2.5 mL of acetone) was added slowly to produce a reaction mixture. The reaction mixture was stirred at room temperature for 1 h and the solid precipitate that was formed was separated by filtration. The obtained crystalline Etravirine ethanesulfonate salt was characterized by PXRD as shown in FIG. 11.

The solid product was suspended in 12.5 mL of acetone. 10% Aqueous NaOH (0.5 mL, 1.2 eq) was added dropwise to form a solution. The solution was stirred for 30 minutes at room temperature, and then 2.5 mL of water was added, whereupon crystallization began. The resulting mixture was stirred for 1 h at 0-5° C. The crystalline solid was separated by filtration and dried under vacuum for 5 h at 50° C. Yield of purified ETV: 390 mg (78%); HPLC purity: 99.80 area %.

We claim:

1. The compound, 4-(2,6-dichloropyrimidin-4-yloxy)-3,5-dimethyl-benzonitrile ("ETHER"), or a salt thereof, of the following formula:

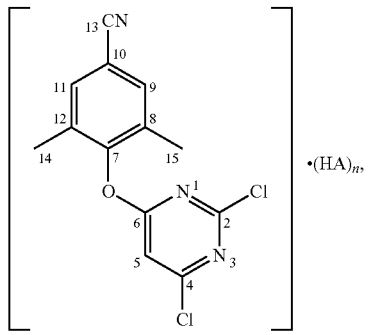

wherein n is either 0 or 1 and HA is an acid.

2. The compound 4-(4,6-dichloropyrimidin-2-yloxy)-3,5-dimethylbenzonitrile ("ETHER C-2 isomer"), or a salt thereof, of the following formula:

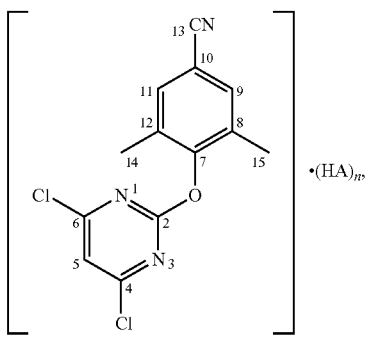

wherein n is either 0 or 1 and HA is an acid.

3. A crystalline form of a mixture of the compounds, 4-(2,6-dichloropyrimidin-4-yloxy)-3,5-dimethylbenzonitrile and 4-(4,6-dichloropyrimidin-2-yloxy)-3,5-dimethylbenzonitrile, characterized by a PXRD pattern having peaks at about 8.0, 11.2, 13.1, 13.8 and 24.2±0.2 degrees two-theta.

4. The crystalline form of claim 3, further characterized by a PXRD pattern having additional peaks at about 11.9, 17.4, 19.6, 26.7 and 30.4±0.2 degrees two-theta.

5. A process for preparing the compound 4-(2,6-dichloropyrimidin-4-yloxy)-3,5-dimethylbenzonitrile, its mixture with 4-(4,6-dichloropyrimidin-2-yloxy)-3,5-dimethylbenzonitrile, or salts thereof, said process comprising reacting 2,4,6-trihalopyrimidine (ThalP) of the following structure:

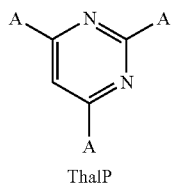

ThalP and 4-hydroxy-3,5-dimethylbenzonitrile (DMHB); wherein each A is independently a halogen.

6. The process of claim 5, wherein said process is carried out in the presence of a solvent.

7. The process of claim 6, wherein the solvent is a mixture of water and a water miscible organic solvent comprising a $C_1$-$C_3$ ketone.

8. The process of claim 6, wherein the water miscible organic solvent is acetone.

9. The process of claim 5, wherein said process is carried out in the presence of a base.

10. The process of claim 9 wherein the base is an inorganic base.

11. The process of claim 10, wherein the inorganic base is an alkali metal base.

12. The process of claim 11, wherein the alkali metal base is sodium hydroxide.

13. The process of claim 5, further comprising recovering from the reaction mixture the compound 4-(2,6-dichloropyrimidin-4-yloxy)-3,5-dimethylbenzonitrile or its mixture with 4-(4,6-dichloropyrimidin-2-yloxy)-3,5-dimethylbenzonitrile or salts thereof.

14. A process for preparing the compound 4-(6 chloro-2-(4-cyanophenylamino)pyrimidin-4-yloxy)-3,5-dimethyl-benzonitrile (ARCPBN):

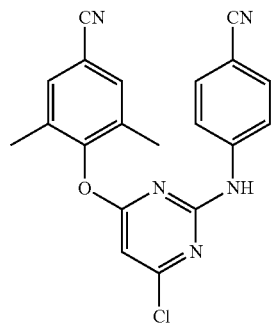

comprising reacting the compound 4-(2,6-dichloropyrimidin-4-yloxy)-3,5-di-methylbenzonitrile or its mixture with 4-(4,6-dichloropyrimidin-2-yloxy)-3,5-dimethylbenzonitrile or a salt thereof and 4-aminobenzonitrile (ABN).

15. The process of claim 14, wherein said process is carried out in the presence of a solvent.

16. The process of claim 15, wherein the solvent is a polar aprotic organic solvent.

17. The process of claim 16 wherein the polar aprotic solvent is dimethylacetamide.

18. The process of claim 14, wherein said process is carried out in the presence of a base.

19. The process of claim 18, wherein the base is an inorganic base.

20. The process of claim 19, wherein the inorganic base is a metal hydride base.

21. The process of claim 20, wherein the metal hydride base is sodium hydride.

22. The process of claim 14, further comprising recovering from the reaction mixture the compound ARCPBN 4-(6-chloro-2-(4-cyanophenyl-amino)pyrimidin-4-yloxy)-3,5-dimethylbenzonitrile.

23. A process for preparing the compound 4-(2,6-dichloropyrimidin-4-yloxy)-3,5-dimethylbenzonitrile, its mixture with 4-(4,6-dichloropyrimidin-2-yloxy)-3,5-dimethylbenzonitrile, or salts thereof, said process comprising reacting 2,4,6-trisubstituted-pyrimidine (TsubP) of the following structure:

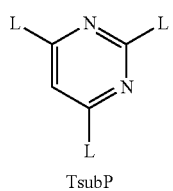

TsubP and 4-hydroxy-3,5-dimethylbenzonitrile (DMHB); wherein each L is independently a leaving group.

24. The process of claim 23, wherein the leaving group is selected from halogens and sulfonyl esters.

25. The process of claim 24, wherein the leaving group is selected from Br, Cl, I, mesylate, tosylate and triflate.

26. The crystalline form according to claim 3, further characterized by a PXRD pattern substantially as depicted in FIG. 3.

* * * * *

UNITED STATES PATENT AND TRADEMARK OFFICE
CERTIFICATE OF CORRECTION

PATENT NO. : 8,153,790 B2
APPLICATION NO. : 13/131698
DATED : April 10, 2012
INVENTOR(S) : Irena Krizmanic et al.

Page 1 of 1

It is certified that error appears in the above-identified patent and that said Letters Patent is hereby corrected as shown below:

On the face of the patent below Item (76) insert

-- (73) Assignee: Teva Pharmaceutical Industries Ltd.,
Petah Tiqva, Israel --

Signed and Sealed this
Twenty-eighth Day of August, 2012

David J. Kappos
*Director of the United States Patent and Trademark Office*